United States Patent [19]

Simmen

[11] Patent Number: 5,333,760
[45] Date of Patent: Aug. 2, 1994

[54] DISPENSING AND MIXING APPARATUS

[75] Inventor: Christen Simmen, Brooklyn, N.Y.

[73] Assignee: Coltene/Whaledent, Inc., Mahwah, N.J.

[21] Appl. No.: 997,679

[22] Filed: Dec. 28, 1992

[51] Int. Cl.$^5$ .............................................. B67D 5/52
[52] U.S. Cl. ................................... 222/137; 222/145; 222/327; 366/184
[58] Field of Search ............... 222/325, 326, 327, 137, 222/145, 136, 135; 366/184, 336

[56] References Cited

U.S. PATENT DOCUMENTS

| | | | |
|---|---|---|---|
| 2,816,518 | 12/1957 | Daggett | 222/145 |
| 4,014,463 | 3/1977 | Hermann | 222/145 |
| 4,117,551 | 9/1978 | Books et al. | 222/148 X |
| 4,240,566 | 12/1980 | Bergman | 222/135 |
| 4,432,469 | 2/1984 | Eble et al. | 222/134 |
| 4,538,920 | 9/1985 | Drake | 222/137 X |
| 4,690,306 | 9/1987 | Stäheli | 222/327 X |
| 4,747,517 | 5/1988 | Hart | 222/137 |
| 4,753,536 | 6/1988 | Spehar et al. | 222/494 X |
| 4,767,026 | 8/1988 | Keller et al. | 222/137 |
| 4,771,919 | 9/1988 | Ernst | 222/145 X |
| 4,869,400 | 9/1989 | Jacobs | 222/137 |
| 4,978,336 | 12/1990 | Capozzi et al. | 222/137 X |
| 4,981,241 | 1/1991 | Keller | 222/145 X |
| 4,989,758 | 2/1991 | Keller | 222/137 |
| 4,995,540 | 2/1991 | Colin et al. | 222/137 X |
| 5,022,563 | 6/1991 | Marchitto et al. | 222/327 |
| 5,033,650 | 7/1991 | Colin et al. | 222/137 |
| 5,038,963 | 8/1991 | Pettengill et al. | 222/137 X |
| 5,065,906 | 11/1991 | Maeder | 222/137 |
| 5,080,262 | 1/1992 | Herold et al. | 222/135 |
| 5,249,862 | 10/1993 | Herold et al. | 222/137 X |

Primary Examiner—Andres Kashnikow
Assistant Examiner—Anthoula Pomrening
Attorney, Agent, or Firm—Helfgott & Karas

[57] ABSTRACT

A dispensing and mixing apparatus for simultaneously dispensing from a cartridge into a static mixing element components which harden when mixed. The components exit the cartridge into the mixing element without intermixing as the components leave the cartridge. The initial intermixing of the components takes place within the mixing element. The cartridge is reusable since the components do not become mixed and harden as they come out of the cartridge. The chambers in the cartridge are of semi-cylindrical configuration and have rounded corners. Ribs can be provided on the cartridge for stiffening the cartridge from deforming under extrusion.

18 Claims, 3 Drawing Sheets

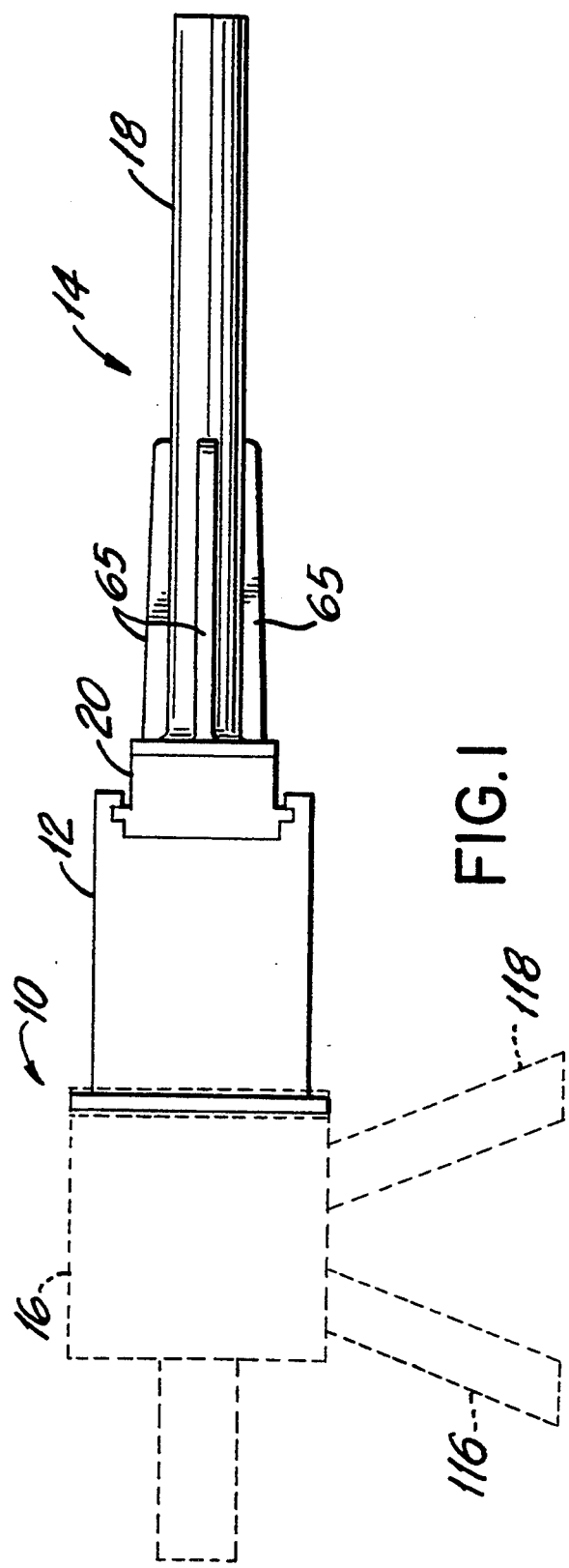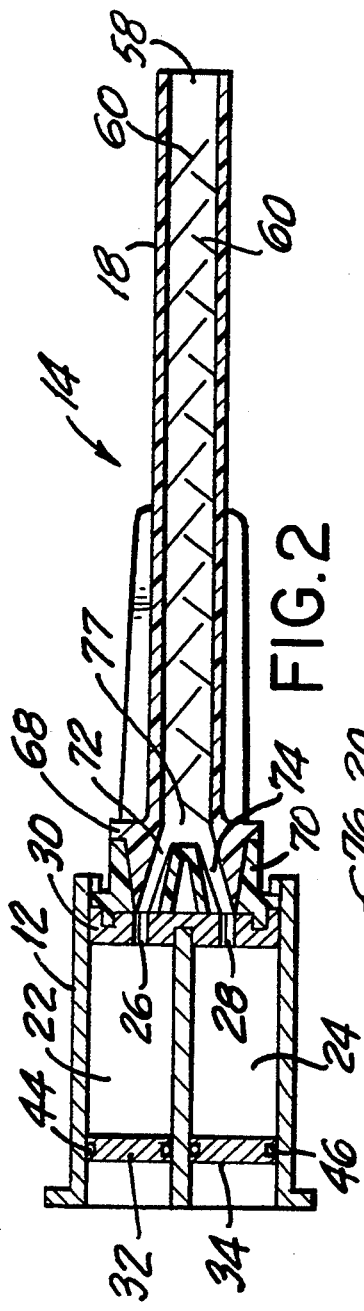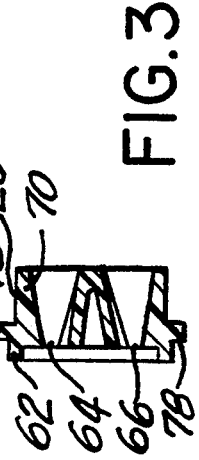

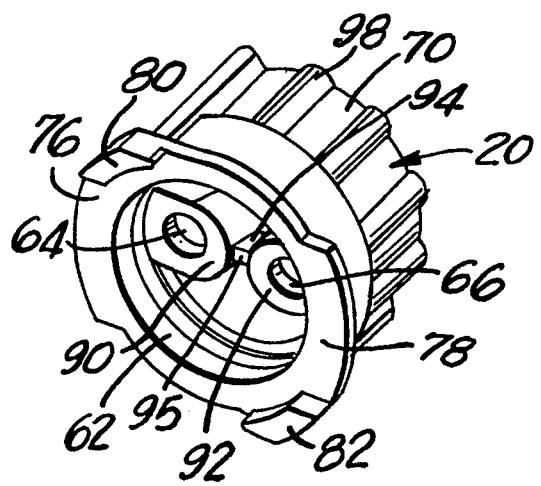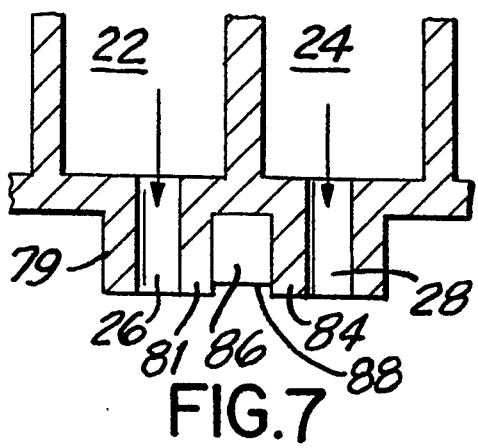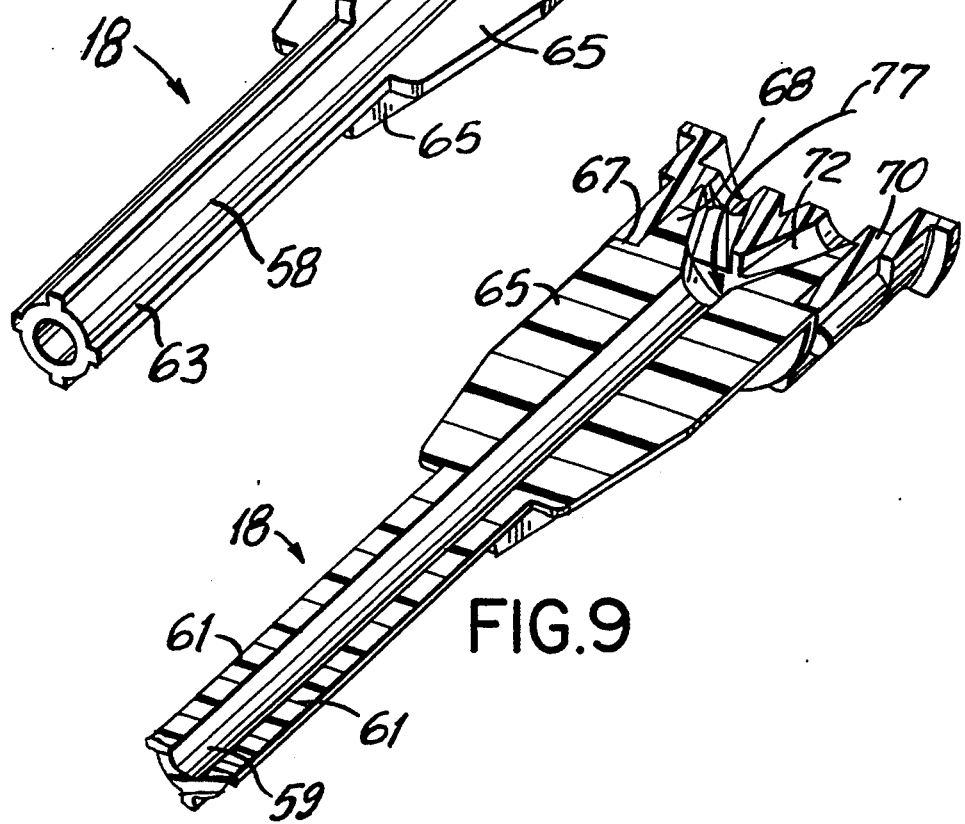

DISPENSING AND MIXING APPARATUS

BACKGROUND OF THE INVENTION

This invention relates to a dispensing and mixing apparatus and more particularly to a unique and simplified structure which permits a dispensing cartridge to be reused with multiple static mixers. In addition, this invention relates to a cartridge structure which can withstand high extrusion pressure while minimizing the thickness of the walls of the cartridge and which can withstand increased extrusion pressure transmitted by the piston. Furthermore, the cartridge includes chambers shaped to facilitate retaining of the materials within the chambers.

Dispensing and mixing apparatus is well known in the prior art for a variety of pasty or highly viscous products such as adhesives, joint filler agents, foams, sealants and molding compounds. The products typically consist of two or more components stored separately in separate chambers in a cartridge. A plunger is usually advanced against a piston in each chamber to extrude the components through orifices into a disposable static mixer removably coupled to the cartridge. As the components flow through the mixer, they are thoroughly intermixed and a chemical reaction is started between the components which ultimately results in a hardening or solidification of the components when they are inserted into the parts to be sealed.

The solidification takes a predetermined amount of time and as such, the components will solidify in time if left in the static mixer and this will render the static mixer no longer useable. If the components get in contact with each other at the exit end of the chambers in the cartridge or in or on any extension of the chambers after the static mixer is removed, the components being in contact will harden and solidify requiring removal of the solidified material, if possible. Occasionally, such solidified material cannot be removed, making it impossible to reuse the cartridge with another mixer, even though the cartridge has not been used up. This has resulted in wasted material because the cartridges have to be disposed of after each use. In areas where the extruded materials are expensive, such as in the dental field, this waste is particularly undesirable.

There have been attempts to solve the problem of avoiding the hardening of material at the end of the cartridge to prevent rendering the cartridge unsuitable for further use. One example of a highly complex and expensive structure for solving this problem is disclosed in U.S. Pat. No. 5,080,262 issued Jan. 14, 1992. This patent discloses a structure in which two components are stored in separate chambers in a cartridge. As the components are extruded from the cartridge, one component is moved into an annular orifice which surrounds a central cylindrical orifice for the other component. A static mixer is provided which screws into the cartridge and has various walls and edges at different levels and of complex shapes required to mate with complementary walls and edges on the coaxial end of the cartridge to form continuations of the annular orifice and the central cylindrical orifice. The complex structure renders the static mixer very expensive and after each use it may be necessary to dispose of the mixer if the components will harden in the mixer. Additionally, by changing the path of the material in the cartridge from colinear to coaxial requires extra pressure.

U.S. Pat. No. 4,767,026 issued Aug. 30, 1988, describes a dispensing and mixing apparatus in which two components to be mixed are stored in separate chambers in a cartridge. A doubled walled baffle is positioned in a common orifice to keep the components separated as they are extruded into a mixer. However, the mixing takes place at the end of the baffle which is at the edge of the cartridge. Typically, after extrusion for a particular use is completed, the static mixer is retained as a cap until the next use. However, since there is no particular structure to keep the components from mixing at the end of the baffle, the back curing of the components upstream of the static mixer will cause the components to harden and the cartridge will have to be discarded together with any unused materials. This apparatus is typical of many prior art in that a thin separation baffle is housed in the cartridge between the component holding chambers and wherein the mixing of the two components occurs at the end of the baffle which is at the end of the cartridge.

The cartridges are typically made of plastic material which is always porous to some extent, and therefore gases and moisture slowly permeate through the outer walls of the plastic cartridges into the chambers. Certain components such as those used in dentistry are contaminated by such gases and are highly reactive to moisture. The greater the exposed surface area of the cartridge, the greater the amount of gas and moisture that will enter the chamber by a given wall thickness.

Additionally, with the continuous pressure applied by the piston, the walls of the cartridge may tend to deflect. In order to combat this deflection, the walls of the chambers are typically made relatively thick. The plastics used are not generally biodegradable and are an environmental problem since the cartridges are not recycled.

In addition, in high pressure extrusion, there is often leakage of the components around the piston which limits the pressure available. Furthermore, the leakage can render the device used to advance the pistons unusable for further applications.

Also, the coupling arrangement between the static mixer and the cartridge was often complex requiring screw threads or clamping arrangements. This provided for time lost in making quick connections and prevented the ability to easily use static mixers with existing cartridges.

In view of the foregoing, a simplified structure which permits the reuse of a cartridge would be very beneficial. These improvements would be particularly beneficial if the cartridge had unique features such as increased strength to withstand deflection under pressure, while at the same time the weight and thickness of the cartridge is maintained at a minimum. In addition, the ability to readily withstand high extrusion pressures without component leakage would be very desirable as would an improved coupling arrangement between the static mixer and the cartridge.

SUMMARY OF THE INVENTION

Accordingly it is an object of the invention to provide a new and improved dispensing and mixing apparatus.

It is another object of the invention to provide a disposable cartridge, which can be used for dispensing viscous components with multiple static mixers.

It is a further object of the invention to provide a dispensing cartridge which keeps the dispensed components from mixing as they are dispensed from the cartridge.

It is still another object of the present invention to provide a dispensing cartridge for high pressure dispensing of components.

It is still a further object of the present invention to provide a mixing apparatus in which the separately dispensed components are maintained separate as they enter the static mixer.

It is another object of the present invention to provide a cartridge which can withstand high pressure with reduced deflection with minimum thickness walls.

It is still another object of the invention to provide an interface between a cartridge and a static mixer which directs the separated components exiting from the cartridge and provides for mixing of the components in the static mixer.

Briefly in accordance with the present invention there is provided a substantially cylindrical cartridge with separate viscous component holding chambers. Each chamber has a cross sectional configuration which is almost semi-cylindrical but with rounded corners at the junction wall between the chambers. The chambers each receive a similarly shaped piston at one end. The semi-cylindrical shape reduces the outer exposure of material to penetration of moisture and gases. The rounded corners permit an easier and better engagement of the piston and the chambers to improve the sealing thereby accommodating greater extrusion pressure.

The other end of each chamber is provided with an exit orifice, which orifices are spaced to avoid components from mixing. The walls of the cartridge are typically made of plastic and are provided with outer ribs to prevent the walls from excess deflection during extrusion. The spacing of the ribs conforms to the deflection changes along the length of the cartridge.

The exit end of the cartridge is provided with a bayonet lock into which a static mixer is secured. The locking structure aligns the exit orifices with inlet orifices in the mixer so that the extruded components are kept separate and do not mix as they exit the chambers. The static mixer includes an adapter section which spaces the mixing of the components from the cartridge end a sufficient amount to avoid back curing of the components into the cartridge.

The aforementioned objects, features and advantages of the invention will, in part, be pointed out with particularity, and will, in part, become obvious from the following more detailed description of the invention taken, in part, with the drawings which form an integral part thereof.

BRIEF DESCRIPTION OF THE DRAWINGS

In the drawings:

FIG. 1 is a schematic view of a dispensing and mixing apparatus made in accordance with the principles of the present invention;

FIG. 2 is a schematic cross sectional view explaining the dispensing and mixing apparatus shown in FIG. 1;

FIG. 3 is a schematic cross section view explaining the mixer adapter shown in FIG. 2;

FIG. 6 is a perspective view of the mixer adapter section showing the coupling arrangement of the mixer adapter which would couple to the cartridge;

FIG. 7 is a schematic drawing showing in cross section the exit from the cartridge wherein the components are separated;

FIG. 8 is a perspective view of the static mixer; and

FIG. 9 is a cross-sectional view taken along line 8—8 of FIG. 8.

DETAILED DESCRIPTION OF THE PREFERRED EMBODIMENT

Figure 4:
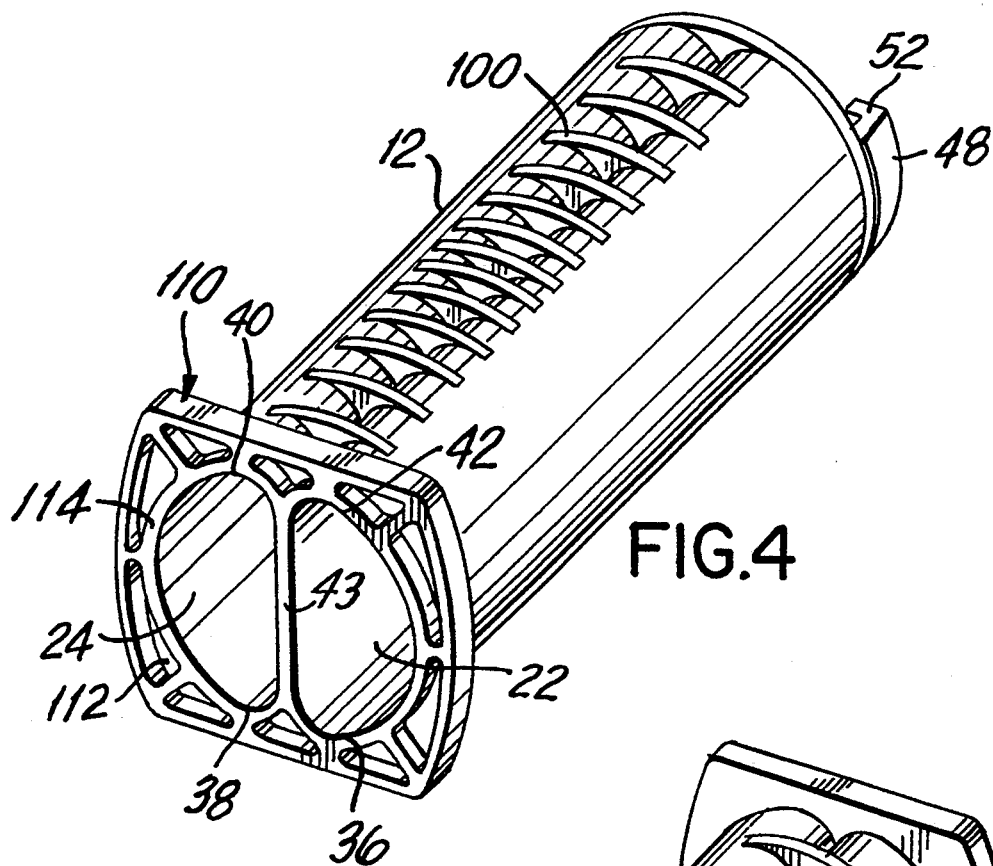
FIG. 4 is a perspective view of the cartridge showing a rib construction for reducing deflection and equalizing over the cartridge length, and taken from the rear flange end.

Referring now to the drawings, there is shown in FIG. 1 a dispensing and mixing apparatus generally designated as 10. The apparatus 10 includes a cartridge 12 and a static mixer generally designated 14. A dispenser with plunger 16 is schematically shown and is used for extruding viscous components from the cartridge, as will hereinafter be described. The cartridge 12 and the mixer 14 are typically made of plastic. The mixer consists of two sections which are a static mixer 18 and a mixer adapter 20. The interior of the static mixer is well known in the art of mixing extruded components and could be of various types as for example described in U.S. Pat. Nos. 4,538,920; 3,923,288, 3,635,444, or others. Although the description will be in terms of a cartridge with two chambers, the cartridge may have more chambers for simultaneously extruding more than two components.

Referring to FIG. 2, the cartridge 12 is shown with two chambers 22, 24 in which viscous components are stored. The components are typically the elements of adhesives, putty, dental impression material, sealants and other dental compounds which when mixed chemically react to start a hardening or solidification process. Each chamber 22, 24 is open at its left end. Before the chambers are filled with components, the orifices 26, 28 at the opposite end are plugged closed with a typical sealing plug (not shown). At the time of filling, the cartridge 12 is not attached to the mixer 14. After the chambers are filled with components, pistons 32, 34 are inserted into the open end of each chamber 22, 24 respectively, to retain the components in the chambers.

Referring to FIG. 4, each chamber 22, 24 has a substantially semi-cylindrical shape. However, the corners 36, 38, 40, 42 which would typically have a sharp edge, have been rounded so that the chambers provide an inwardly turned bend at the two ends toward the junction wall 43. Pistons 32, 34 would have the same shape as the chambers in which they fit. Each piston 32, 34 as shown in FIG. 2 is provided with a rubber O-ring 44, 46 respectively, in a notch. The lack of sharp edges permits a tight seal between the pistons and the walls of the chambers. Furthermore, as will be described, the semi-cylindrical construction desires the use of ribs to reinforce the walls of the chambers in order to reduce deflections or for a given deflection it allows the use of thinner outer walls of the cartridge for a given extrusion pressure. By using a semi-cylindrical shape for the chamber, there is a lesser amount of exterior surface of the chambers which is exposed to gases and moisture from the environment.

Figure 5:
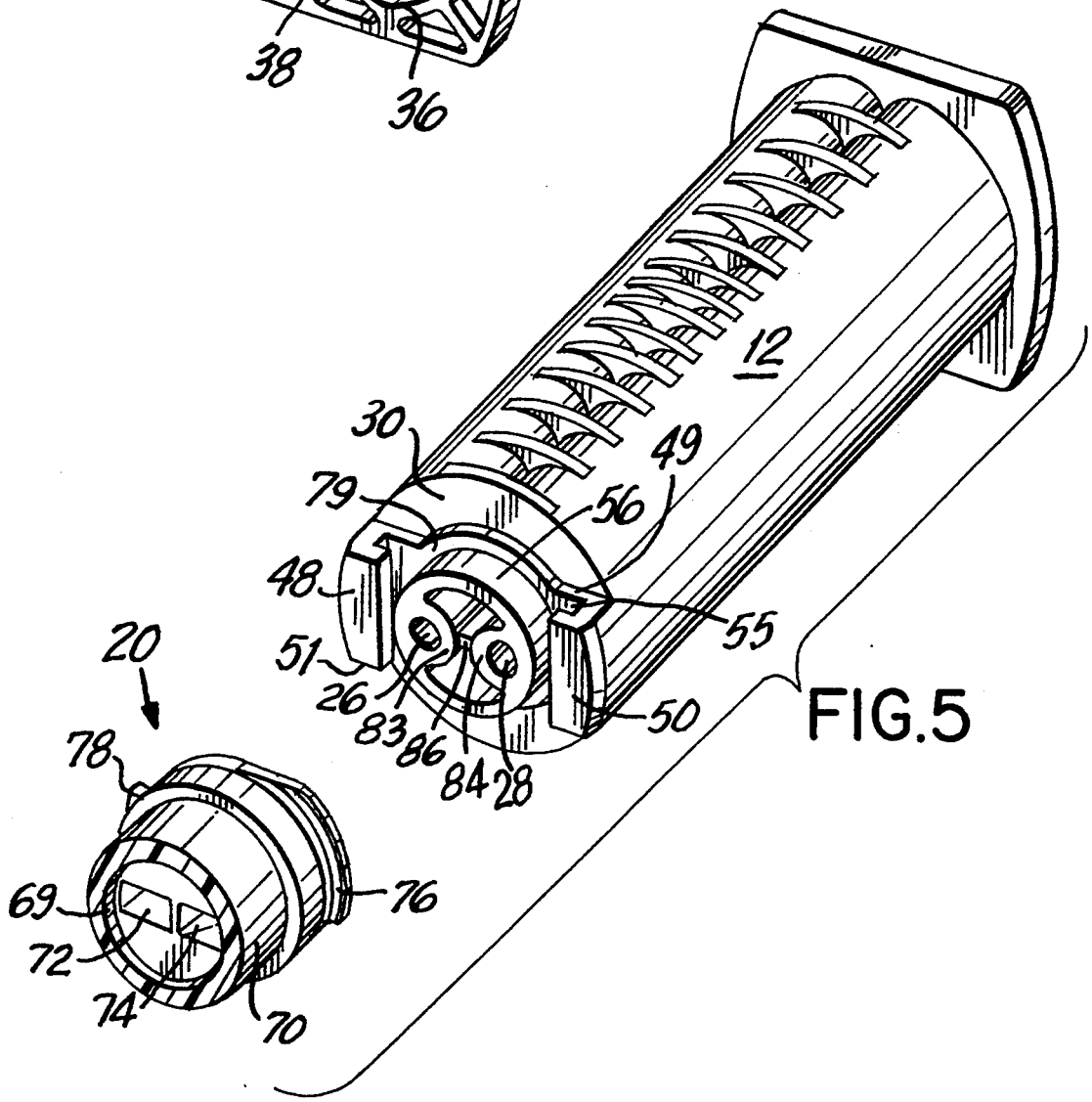
FIG. 5 is an exploded perspective view showing the cartridge at its coupling end to the mixer, and showing the mixer adapter section which would couple to the cartridge.

Referring to FIG. 5, the coupling end 30 of the cartridge 12 is shown. The coupling end 30 includes two bayonet type mounts 48, 50 into which mixer adapter 20 locks. Also, the thickness of each mount 48, 50 increases from the entrance side 55 of each mount to the opposite ends. In addition, end wall 30 includes a raised projection 56 which, as will be described, is used for aligning the mixer adapter 20 with the orifices 26, 28.

As shown in FIGS. 2, 8 and 9, the static mixer 18 consists of a tube 58 and a plurality of stationary mixing vanes 60 internally of the tube, as are well known in the art. The vanes 60 can be of various shapes and cause the components being forced through the tube 58 to thoroughly mix together. The static mixer is formed of two sections, one of which is shown in FIG. 9. The sections include a central cylindrical channel 59 and can include outwardly extending flanges 61 on either side forming the support ribs 63. Wider rib sections 65 can also be formed on the upper section at 90 degree angles to each other to provide further support. These outwardly extending rib sections permit grasp of the mixer tube and provide the enforcement to the mixer tube upon the occurrence of extrusion pressures.

A mixer adapter section 20, as shown in FIGS. 5 and 6, is coupled, by way of example through sonically welded, to the static mixer section 18 along the weld line 67 by welding the face 69 (FIG. 5) to the flange 71 (FIG. 8). The mixer adapter 20 has on its coupling end an annular recess 62 which is sized to receive the projection 56 in the cartridge end 30. Two orifices 64, 66 are positioned in the recess 62 of the mixer adapter 20 and are of the same diameter as orifices 26, 28 in the cartridge end 30 and are positioned to align with the orifices 26, 28. As shown in FIGS. 2, 3 and 9, the receiving end 68 of the mixer tube fits within the outer wall 70 of the mixer adapter 20 to form passageways 72, 74 which extend from orifices 64, 66 respectively and converge in the static mixer whereby the junction point of the components occurs at point 77. As shown in FIG. 6, mixer adapter 20 has lips 76, 78 which are inserted into bayonet mounts 48, 50 and edges 80, 82 which form the stops against the tops of the mounts 49, 51 (FIG. 5) when the mixer adapter is locked into place. The mixer adapter is axially inserted into the cartridge and as the lips are rotated behind the mounts 48, 50, the lips are progressively squeezed tighter by the thickening mounts 48, 50 to hold the orifices in the cartridge and adapter tightly together. The combination of the bayonet mounts with a positive stop and the mating projection 56 and recess 62 assure the alignment of the orifices in the mixer adapter with the orifices in the cartridge.

As best noted in FIGS. 5, 6 and 7, the projection 56 includes an outer peripheral circular wall 79 which supports the orifices 26, 28 by means of an outer protecting wall 83 and 84. There is defined therebetween a supporting spacer wall 86. However, it would be noted that the spacer wall 86 is recessed slightly below the walls 81, 84 as shown at 88.

A similar arrangement will be noted in FIG. 6 with respect to the mating portion in the recess. There are likewise provided the exterior walls 90, 92 around the orifices 64, 66. A bridging support number 94 provides support between these two sections and it will be noted that it is slightly recessed at a point 95 beneath the two adjoining sections. This recess aids in preventing mixing between the two components until the junction point 71 which is spaced from the cartridge end.

Alternately one of the set of peripheral walls 83 & 84 or 90 & 92 could have a slight raised elevation to provide a locally tighter fit.

It should be appreciated, that the junction point 71 is sufficiently spaced along the static mixer from the terminating end of the cartridge so that when the static mixer is left in place and curing of the materials occurs, there will not be any back curing upstream of the mixer and into the cartridge. Thus, there will not be any blockage of the cartridge exit holes 26, 28 whereby the cartridge will always be ready to use.

As a result, the arrangement provides that the static mixers can be easily mounted onto the ends of the cartridge with axial insertion and a bayonet lock arrangement. Furthermore, a positive coupling is provided whereby none of the components will leak from the front end of the cartridge. Furthermore, the static mixer is secured sufficiently so that even under the additional pressure the static mixer will not be ejected from the cartridge but will remain in place.

Of more significance, is the fact that after the static mixer has been used, it can be removed and discarded. The cartridge, however, which typically retains additional components will not have the components mixed at the front face of the cartridge whereby the cartridge will not be clogged at its front face by the co-mixing of the two components. In this manner, the cartridge can be again reutilized with numerous static mixers until all of the contents of the cartridge have been used up.

In order to provide additional retention and easy grasping, a plurality of ribs 98 are placed externally around the mixer adapter section 20.

As shown in FIGS. 4 and 5, the shape of semi-cylindrical chambers 22, 24 in the cartridge provides a space for a series of ribs 100 which strengthen the walls of the chambers against deflections under pressure. This is important since it can then permit thinner walls which reduce the cost of the cartridge and also avoid the use of less plastic. The rib construction permits the thinner walls to withstand a given level of pressure by reduced and equalized deflection over cartridge length. The ribs 100 are spaced closer at the center to minimize deflection over most of the length of the cartridge where the greatest deflection occurs. Alternately a solid sleeve could be placed around the cartridge to contain the deflections.

At the outer end of the cartridge, as shown in FIG. 4, there is an outwardly directed flange portion 110 which can be used to couple to a suitably arranged plunger section. The flange portion includes open spacings 112 to form a plurality of rib sections 114 in the flange structure. In this way the flange structure provides a skeletal but rigid structure and thereby requires less plastic material. However, the flange could also be of a solid construction.

It should be appreciated, that with the semi-cylindrical arrangement, two separate cartridges are provided which are spaced apart by a center wall. This reduces the amount of exposed surface to the external gasses and moisture. At the same time, the overall exterior of the cartridge is circular. In this way appropriate labels can be placed around the circular periphery of the cartridge and given the benefit of packaging and storing ease. At the same time, the semi cylindrical arrangement provides the needed separation of the two chambers. Furthermore, rounding the corners permits a better seal between the chambers and the piston.

In use, a mixer 14 is connected to a filled cartridge 12 with the annular projection 56 in the annular recess 62 and the edges 80, 82 locked against walls of the notches 49, 51. Handles 116, 118 are squeezed to advance pistons 32, 34 against the components in the chambers. The components are extruded out orifices 26, 28 directly into orifices 64, 66. At the point of exit from orifices 26, 28, the components are spaced far apart to avoid any mixing and hardening. The first point of component mixing is at point 71 at the end of passageways 72, 74 in the static mixer 18. When use is completed, the components in the static mixer will harden. The mixer typically remains on the cartridge as a cap until the next use. During this time, back curing upstream of the mixer may occur but it will not reach the cartridge so the exit of the cartridge does not get clogged.

When the device must be used again, the mixer is then removed from the cartridge and the orifices 26, 28 are available to further use with a new static mixer.

There has been described a preferred embodiment of the invention. However, it should be understood that various changes and modifications may be made thereto without departing from the spirit and scope of the invention.

What is claimed is:

1. A dispensing and mixing apparatus for mixing at least two components which react with one another after contact, comprising:
    a cartridge having elongated, parallel, separate chambers for holding the respective components, each chamber having an open end for receiving a piston therein for extruding the component and an outlet orifice in an opposing end of the chamber, separator means at an outer end of the cartridge including the outlet orifices of said chambers and separating them into laterally spaced apart outlet openings so as to prevent contacting of the components at the outer end of the cartridge;
    a disposable mixing element having an inlet end and an outlet end, and including a mixing chamber and adapter means provided at said inlet end and connected to said mixing chamber to be disposed therewith after use, said adapter means having inlet orifices spaced apart for alignment with the outlet orifices of the chambers, said adapter means providing passages communicating with said inlet orifices so as to remote said mixing chamber from said inlet orifices so that the components first contact each other inside the mixing chamber at a point spaced from the inlet orifices;
    and means for aligning and removably locking the adapter means onto the separator means of said cartridge such that the outlet orifices of the chambers and the inlet orifices of the chambers and the inlet orifices of the adapter means of the mixing element are in alignment, so that during extrusion of the components through the outlet orifices the components go directly into the passageways without contacting each other.

2. A dispensing and mixing apparatus according to claim 1, wherein said aligning and locking means includes an annular protrusion on one of said adapter means and said separator means and an annular recess on the other of said adapter means and said separator means for receiving the annular protrusion, to permit axial insertion of the mixing element to the cartridge.

3. A dispensing and mixing apparatus according to claim 2, wherein said aligning and locking means further includes a bayonet type connector which forces the mixing element and cartridge together with the corresponding orifices being aligned.

4. A dispensing and mixing apparatus as in claim 1, wherein said chambers are in parallel spaced relationship with each other, and said outlet orifices are also in parallel spaced relationship with each other, whereby the components are extruded along a linear path.

5. A dispensing and mixing apparatus as in claim 1, wherein each of said outlet orifices in said separator means and each of said inlet orifices in said adapter means are respectively surrounded by a peripheral wall member, each wall member being isolated by a spaced gap from an adjacent wall member within the same means.

6. A dispensing and mixing apparatus as in claim 1, wherein said cartridge is of substantially cylindrical configuration.

7. A dispensing and mixing apparatus as in claim 6, wherein there are two chambers and wherein each chamber is of substantially semi-cylindrical configuration, and comprising a common diametrical separation wall between the chambers.

8. A dispensing and mixing apparatus as in claim 7, wherein the opposing ends of each chamber are rounded toward said separation wall to eliminate sharp edges in the cross sectional configuration of the chambers.

9. A dispensing and mixing apparatus as in claim 8, and further comprising longitudinally spaced apart transverse ribs spanning grooves to provide support against deformation of the cartridge.

10. A dispensing and mixing apparatus as in claim 9, wherein the longitudinal spacing of said ribs is unequal.

11. A dispensing and mixing apparatus as in claim 10, wherein there are a greater number of ribs adjacent the longitudinal center of said cartridge, and a fewer number of ribs adjacent the distal ends of the cartridge.

12. A dispensing and mixing apparatus as in claim 1, wherein said mixing element further comprises a plurality of stiffening ribs projecting radially outwardly therefrom about at least a portion of the length of the mixing element.

13. A dispensing and mixing apparatus as in claim 8, and further comprising pistons for moveable passage through the chambers, and O-rings peripherally around the pistons, whereby the O-rings snugly fit within the rounded cross sectional configuration.

14. A dispensing and mixing apparatus as in claim 1, wherein said cartridge comprises a coupling flange at said open end.

15. A dispensing and mixing apparatus as in claim 14, wherein said flange is of skeletal structure.

16. A dispensing and mixing apparatus as in claim 1, and comprising coupling means at said open end to couple to a dispenser.

17. A dispensing and mixing apparatus as in claim 1, wherein said outlet orifices are substantially parallel to each other.

18. A dispensing and mixing apparatus as in claim 1, wherein said outlet orifices are linearly spaced apart from each other.

* * * * *

UNITED STATES PATENT AND TRADEMARK OFFICE
CERTIFICATE OF CORRECTION

PATENT NO. : 5,333,760
DATED      : August 2, 1994
INVENTOR(S) : Christen Simmen It is certified that error appears in the above-indentified patent and that said Letters Patent is hereby corrected as shown below:

Column 7, lines 50 and 51, delete "chambers and the inlet orifices of the"

Signed and Sealed this

Eleventh Day of June, 1996

Attest:

BRUCE LEHMAN

*Attesting Officer*    *Commissioner of Patents and Trademarks*